United States Patent
Girouard (10) Patent No.: US 7,542,798 B2
(45) Date of Patent: *Jun. 2, 2009

(54) SYSTEM AND METHOD FOR TREATING AN ADVERSE CARDIAC CONDITION USING COMBINED PACING AND DRUG DELIVERY

(75) Inventor: Steven D. Girouard, Woodbury, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 327 days.

This patent is subject to a terminal disclaimer.

(21) Appl. No.: 11/188,832

(22) Filed: Jul. 25, 2005

(65) Prior Publication Data

US 2005/0256543 A1    Nov. 17, 2005

Related U.S. Application Data

(62) Division of application No. 10/017,941, filed on Dec. 12, 2001, now Pat. No. 6,941,168.

(51) Int. Cl.
*A61N 1/362* (2006.01)

(52) U.S. Cl. ............................. 607/3; 607/14
(58) Field of Classification Search ........... 607/3, 607/9–27

See application file for complete search history.

(56) References Cited

U.S. PATENT DOCUMENTS

| 5,925,066 A | 7/1999 | Kroll et al. |
| 5,999,851 A | 12/1999 | White |
| 6,361,522 B1 | 3/2002 | Scheiner et al. |
| 6,453,195 B1 | 9/2002 | Thompson |
| 6,471,645 B1 | 10/2002 | Warkentin et al. |

*Primary Examiner*—Scott M Getzow
(74) *Attorney, Agent, or Firm*—Hollingsworth & Funk, LLC (57) ABSTRACT

A system and method of treating an adverse cardiac condition, such as cardiac arrhythmia or a non-arrhythmic event, involves producing, by use of a patient actuatable non-implanted activator, an activation signal in response to a patient sensing a perceived adverse cardiac condition. The method further involves confirming, by an implantable medical device provided within the patient, that the patient is experiencing an actual adverse cardiac condition. A perceivable initiating signal instructing the patient or a physician to commence with a drug delivery regimen to treat the actual cardiac adverse condition is generated by the non-implanted activator. In one approach, the implantable medical device operates in a safe mode of pacing during drug treatment of the actual adverse cardiac condition. In another approach, an appropriate pacing, cardioversion or defibrillation regimen is initiated to treat the actual adverse cardiac condition.

20 Claims, 8 Drawing Sheets

SYSTEM AND METHOD FOR TREATING AN ADVERSE CARDIAC CONDITION USING COMBINED PACING AND DRUG DELIVERY

RELATED PATENT DOCUMENTS

This is a divisional of U.S. patent application Ser. No. 10/017,941 filed on Dec. 12, 2001, now U.S. Pat. No. 6,941,168, to which Applicant claims priority under 35 U.S.C. § 120, and which is incorporated herein by reference.

FIELD OF THE INVENTION

The present invention relates generally to implantable medical devices and, more particularly, to the treatment of cardiac arrhythmia by combined pacing and drug delivery through use of a non-implantable activator device in concert with an implantable cardiac management device.

BACKGROUND OF THE INVENTION

Proper cardiac function relies on the synchronized contraction of the heart at regular intervals. When normal cardiac rhythm is initiated at the sinoatrial node, the heart is said to be in sinus rhythm. However, when the heart experiences irregularities in its coordinated contraction, due to electrophysiologic disturbances caused by a disease process or from an electrical disturbance, the heart is denoted to be arrhythmic. The resulting cardiac arrhythmia impairs cardiac efficiency and can be life-threatening.

Cardiac arrhythmias originating in the atria of the heart are called supra-ventricular tachyarrhythmias (SVTs). SVTs take many forms, including atrial fibrillation and atrial flutter. Both conditions are characterized by rapid, uncoordinated contractions of the atria. Besides being hemodynamically inefficient, the rapid contractions of the atria can also adversely affect the ventricular rate. This occurs when the aberrant impulse in the atria are transmitted to the ventricles. It is then possible for the aberrant atrial signals to cause irregular ventricular activation and even induce ventricular tachyarrhythmias.

Cardiac arrhythmias occurring in the ventricular region of the heart, by way of further example, are called ventricular tachyarrhythmias. Ventricular tachycardia (VTs), for example, are conditions denoted by a rapid heart beat, 150 to 250 beats per minute, that has its origin in some abnormal location with the ventricular myocardium. The abnormal location typically results from damage to the ventricular myocardium from a myocardial infarction. Ventricular tachycardia can quickly degenerate into ventricular fibrillation (VF). Ventricular fibrillation is a condition denoted by extremely rapid, non synchronous contractions of the ventricles. This condition is fatal unless the heart is returned to sinus rhythm within a few minutes.

Pro-arrhythmia has been defined as the provocation of a new arrhythmia or the aggravation of a pre-existing arrhythmia during therapy with a drug at doses or plasma concentrations below those considered toxic. Suggested criteria for pro-arrhythmia include: the new appearance of a sustained ventricular tachyarrhythmia; change from a nonsustained to a sustained ventricular tachyarrhythmia; acceleration of tachycardia rate; or the new appearance of a clinically significant bradyarrhythmia or conduction defect. Pro-arrhythmia can be the direct result of a drug's electrophysiologic effects on conduction velocity, refractoriness, and automaticity. However, it may also be the result of metabolic abnormalities, changes in autonomic state, or drug/drug interactions that amplify or alter the drug's electrophysiologic effects.

SVT Atrial Fibrillation (AF) is the most common arrhythmia in man. AF may be terminated by defibrillation shocks or by anti-arrhythmic drugs. Defibrillation shocks are successful at terminating AF in the majority of patients, however, they have physical/psychological side effects of pain or discomfort, low patient tolerance, and the potential for ventricular pro-arrhythmia. Anti-arrhythmic drugs can also be highly successful at terminating AF. However, drugs present a significant risk of ventricular pro-arrhythmia in the hours-days following chemical cardioversion. The ventricular pro-arrhythmia observed following attempted (successful or unsuccessful) chemical cardioversion of AF is typically polymorphic ventricular tachycardia (e.g., Torsade-de-Pointes). Torsade is known to be exacerbated by ventricular pauses and bradycardia. Importantly, Torsade-de-Pointes can be prevented by pacing modes that eliminate ventricular pauses and bradycardia.

AF patients who are candidates for cardioversion have frequent or recurring episodes of AF and therefore will require future electrical or chemical cardioversion to maintain normal sinus rhythm. Chemical cardioversion may allow for the alleviation of AF burden with elimination of the single largest drawback of defibrillation therapy—patient pain perception. However, the pro-arrhythmia risk associated with chemical cardioversion is significant (~5%). As a result, following chemical cardioversion, patients may remain in the hospital for some number of hours or days to be monitored for the presence of ventricular arrhythmias.

There exists a need for improved systems and methods for treating cardiac arrhythmias and other adverse cardiac conditions, including adverse non-arrhythmic conditions. There exists a further need for such systems and methods that address the increased risk of pro-arrhythmia following delivery of chemical cardioversion. The present invention fulfills these and other needs.

SUMMARY OF THE INVENTION

The present invention is directed to methods and systems for treating an adverse cardiac condition. According to one embodiment, an activation signal is generated by a patient actuatable non-implanted activator in response to the patient sensing a perceived adverse cardiac condition. An implantable medical device implanted within the patient confirms that the patient is experiencing an actual adverse cardiac condition. The non-implanted activator, in communication with the implantable medical device, generates a perceivable initiating signal instructing commencement of a drug delivery regimen to treat the actual adverse cardiac condition. A safe mode of pacing appropriate for the adverse cardiac condition is initiated.

The activation signal is produced in response to the patient sensing the perceived adverse cardiac condition or in response to the implantable medical device sensing the actual adverse cardiac condition. The safe mode of pacing is a pacing mode appropriate for the drug delivered to the patient and the current condition of the patient. The safe mode of pacing preferably terminates in response to expiration of a predefined timeout period. The predefined timeout period is preferably associated with a half-life of a drug delivered to the patient or a sensed resolution of the adverse cardiac condition.

Initiating the safe mode of pacing typically involves pacing one, two, three or four chambers of the patient's heart in accordance with a selected safe pacing mode. The safe mode of pacing may be changed to another mode of pacing in response to an effect of the drug delivery regimen on the patient. Also, the safe mode of pacing may be changed to another mode of pacing in response to an effect of the safe mode of pacing on the patient. After termination of the actual adverse cardiac condition, a pacing mode considered normal for the patient is initiated.

In accordance with another embodiment of the present invention, a system for treating cardiac arrhythmia or other adverse cardiac condition includes a non-implanted activator actuatable by a patient or physician that operates in cooperation with an implantable medical device implanted within a patient. The activator includes a communication unit and produces an activation signal in response to a patient sensing a perceived adverse cardiac condition. Alternatively, or in addition, the activation signal may be produced by the non-implanted activator in response to the implantable medical device detecting the cardiac condition. The implantable medical device includes communication circuitry for communicating with the non-implanted activator.

The detection and therapy delivery system of the implantable medical device includes a lead system for detecting cardiac signals and delivering therapies to the heart. Such therapies may include cardiac pacing, cardioversion or defibrillation. A control system of the implantable medical device, in response to the activation signal, confirms that the patient is experiencing an actual adverse cardiac event and generates a confirmation signal. The control system initiates a pacing regimen to protect against pro-arrhythmic conditions, and the non-implantable activator generates a perceivable initiating signal instructing the patient or a physician to commence with a drug delivery regimen to treat the actual adverse cardiac condition.

The control system, in one configuration, terminates the pacing regimen in response to expiration of a predefined timeout period. The predefined timeout period is preferably associated with the half-life of the drug or drugs used in the drug delivery regimen. For example, the predefined timeout period may represent a duration of time of at least twice as long as one half-life of a drug of the drug delivery regimen. The control system may provide for additional functionality. For example, the control system may initiate electrogram storage in response to the activation signal or the initiating signal.

In one embodiment, the control system initiates a pacing mode associated with a reduced risk of cardiac (e.g., ventricular) arrhythmia for the drug delivery regimen. For example, the drug delivery regimen may include a number of deliverable drugs, and the control system initiates a pacing mode associated with a reduced risk of cardiac arrhythmia for a particular deliverable drug of the drug delivery regimen.

The control system may also change or adjust a mode of the pacing regimen in response to an effect of the drug delivery regimen on the patient. For example, the control system may change or adjust a mode of the pacing regimen after termination of an adverse cardiac condition.

The adverse cardiac condition confirmed by the control system may be an atrial arrhythmic condition. In such a case, the control system terminates the pacing regimen in response to expiration of a predefined timeout period, where the predefined timeout period represents a period of increased risk of ventricular pro-arrhythmia. The pacing regimen preferably includes a regimen to treat ventricular pro-arrhythmia, and the control system initiates a pacing mode associated with a reduced risk of ventricular pro-arrhythmia. For example, the drug delivery regimen may include a number of deliverable drugs. The control system may change a mode of the pacing regimen to a mode associated with a reduced risk of ventricular arrhythmia for a particular deliverable drug of the drug delivery regimen.

In accordance with a further embodiment of the present invention, a method of treating cardiac arrhythmia involves producing, by use of a patient actuatable non-implanted activator, an activation signal in response to a patient sensing a perceived cardiac arrhythmic condition. The method further involves confirming, by communication between the non-implanted activator and an implantable medical device provided within the patient, that the patient is experiencing an actual cardiac arrhythmic condition. A perceivable initiating signal instructing the patient or a physician to commence a drug delivery regimen to treat the actual cardiac arrhythmic condition is generated by the non-implanted activator. A pacing, cardioversion or defibrillation regimen (pacing regimen) is initiated to treat the actual cardiac arrhythmic condition.

In accordance with another embodiment of the present invention, a method of treating atrial arrhythmia involves producing, by use of a patient actuatable non-implanted activator, an activation signal in response to a patient sensing a perceived atrial arrhythmic condition. The method further involves confirming that the patient is experiencing an actual atrial arrhythmic condition. A perceivable initiating signal is then generated by the activator to instruct the patient or a physician to commence with a drug delivery regimen to treat the actual atrial arrhythmic condition. A pacing, cardioversion or defibrillation regimen to treat the actual atrial arrhythmic condition is initiated. The pacing regimen preferably accounts for presence of a drug delivered to the patient as part of the drug delivery regimen.

In accordance with yet another embodiment of the present invention, a method of treating cardiac arrhythmia involves producing, by use of a patient actuatable non-implanted activator, an activation signal in response to sensing a perceived cardiac arrhythmic condition by a patient or an implantable medical device provided within the patient. The method further involves confirming, by communication between the non-implanted activator and the implantable medical device, that the patient is experiencing an actual cardiac arrhythmic condition. A perceivable initiating signal is generated by the non-implanted activator instructing the patient or a physician to commence with a drug delivery regimen to treat the actual cardiac arrhythmic condition.

The method may further involve communicating to the patient a particular drug to administer. A particular dosage of a drug to administer may be communicated to the patient. The method may involve communicating to the patient a plurality of reminders to administer a particular drug at specified times.

According to another embodiment, a method of treating an adverse cardiac condition involves initiating a safe mode of pacing appropriate for treating an adverse non-arrhythmic cardiac event or condition. The safe mode of pacing can involve pacing one or both of the patient's ventricles to improve pumping efficiency of the patient's heart. The adverse cardiac condition can be an episode of angina, a heart failure decompensation event, or an acute ischemic event, for example.

A cardiac management system, according to an embodiment for treating adverse non-arrhythmic cardiac conditions, includes a detection and therapy delivery system for detecting cardiac signals and delivering therapies appropriate to treat such adverse non-arrhythmic cardiac conditions. Such therapies may include cardiac pacing that increases pumping efficiency of the heart. For example, such therapies can include left ventricular pacing or bi-ventricular pacing. A control system of the implantable medical device, in response to an activation signal, confirms that the patient is experiencing an actual adverse non-arrhythmic cardiac event and generates a confirmation signal. The control system initiates a pacing regimen to best address the adverse non-arrhythmic cardiac condition, and the non-implantable activator generates a perceivable initiating signal instructing the patient or a physician to commence with a drug delivery regimen to treat the actual adverse non-arrhythmic cardiac condition.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

The embodiments of the present system illustrated herein are generally described as being implemented in an implantable cardiac defibrillator, which may operate in numerous pacing modes known in the art. The systems and methods of the present invention may also be implemented in other implantable medical devices that sense cardiac activity, such as pacemakers and cardiac monitors, for example. Such implantable medical devices may be single and multiple heart chamber devices. For example, the invention may be implemented using a pacemaker, defibrillator, resynchronizer, cardioverter, or combination of such devices for single or multiple chamber applications. In one particular embodiment, the present invention is implemented in an implantable atrial cardioverter/defibrillator. The systems and methods of the present invention may also be implemented, in part, in external cardioverter/monitor systems, programmers, and other non-implantable systems operable by a physician and/or a patient.

The present invention provides for systems and methods that monitor, moderate, or both monitor and moderate cardiac activity for patients who are taking anti-arrhythmic drugs or other drugs prescribed to treat a patient's anomalous cardiac condition. Systems and methods of the present invention also provide for monitoring, moderation, or both monitoring and moderation of cardiac activity for patients who are suffering from adverse non-arrhythmic heart conditions and taking drugs prescribed to treat adverse cardiac activity associated with such non-arrhythmic heart conditions.

Depending on the nature of the drug regimen, a patient may be susceptible to arrhythmias or other adverse cardiac activity as a side effect of the administered drug. In one embodiment, an implantable medical device provides for selectability between various pacing modes, including pacing modes that account for the increased risk of an arrhythmia developing during the effectiveness period of a particular drug delivered to the patient. In another embodiment, an implantable medical device provides for selectability between various pacing modes to improve pumping efficiency of the heart during the effectiveness period of a particular drug delivered to the patient.

In accordance with another embodiment, a non-implanted activator is used by the patient or physician to interact with the implantable medical device provided within the patient. Upon sensing the onset of a cardiac arrhythmic event or other adverse cardiac condition, the patient actuates the activator which communicatively cooperates with the implantable medical device to confirm the presence of an actual adverse cardiac condition, communicate such confirmation to the patient as a patient perceivable signal indicating that a particular chemical cardioversion drug regimen is to be initiated, and initiate a pacing regimen appropriate for the particular chemical cardioversion drug regimen.

The range of drugs defining a given drug therapy regimen may be varied according to the type and nature of a given patient's particular cardiac condition. In the case of atrial fibrillation, for example, an appropriate drug regimen may include any one or a combination of anti-arrhythmic (AA) agents that have been approved for the chemical treatment of atrial fibrillation. A non-exhaustive, non-limiting list of such AA agents includes: quinidine, procainamide, disopyramide, flecaininde, propafenone, moricizine, sotalol, amiodarone, ibutilide, and dofetilide (e.g., class III anti-arrhythmic agents).

The activator may also be actuated by the patient to selectively initiate and terminate storage of electrograms. The pacing regimen continues for at least a period of time during which the delivered drug influences the patient's cardiac activity, such as a time period defined by several drug half lives. The pacing regimen may, for example, continue beyond the time in which chemical cardioversion terminates the arrhythmic condition. The QT interval may be monitored by the implantable medical device to determine the effectiveness and/or influence of a cardioversion drug delivered to the patient.

The implantable medical device may include at least one atrial and one ventricular pace/sense lead. The pacing modes of the implantable medical device include pacing modes that reduce the likelihood of pro-arrhythmia following attempted chemical cardioversion. For example, the implantable medical device may include rate-smoothing algorithms to prevent ventricular pauses and bradycardia (e.g., VRR, Sudden Brady Response).

In the specific case of atrial fibrillation (AF), for example, the pacing modes include those that provide for a reduced risk of polymorphic ventricular tachycardia onset (e.g., Torsade-de-Pointes) following attempted chemical cardioversion. Torsade-de-Pointes can be prevented by implementing pacing modes that eliminate ventricular pauses and bradycardia. The implantable medical device may provide for the selection of additional operating modes, such as burst pacing modes for tachycardia termination, atrial ATP (antitachycardia pacing) modes, including burst, decrement, and scan modes, and standard pacing modes, such as DDD, VVI, VVIR, among others.

Figure 1:
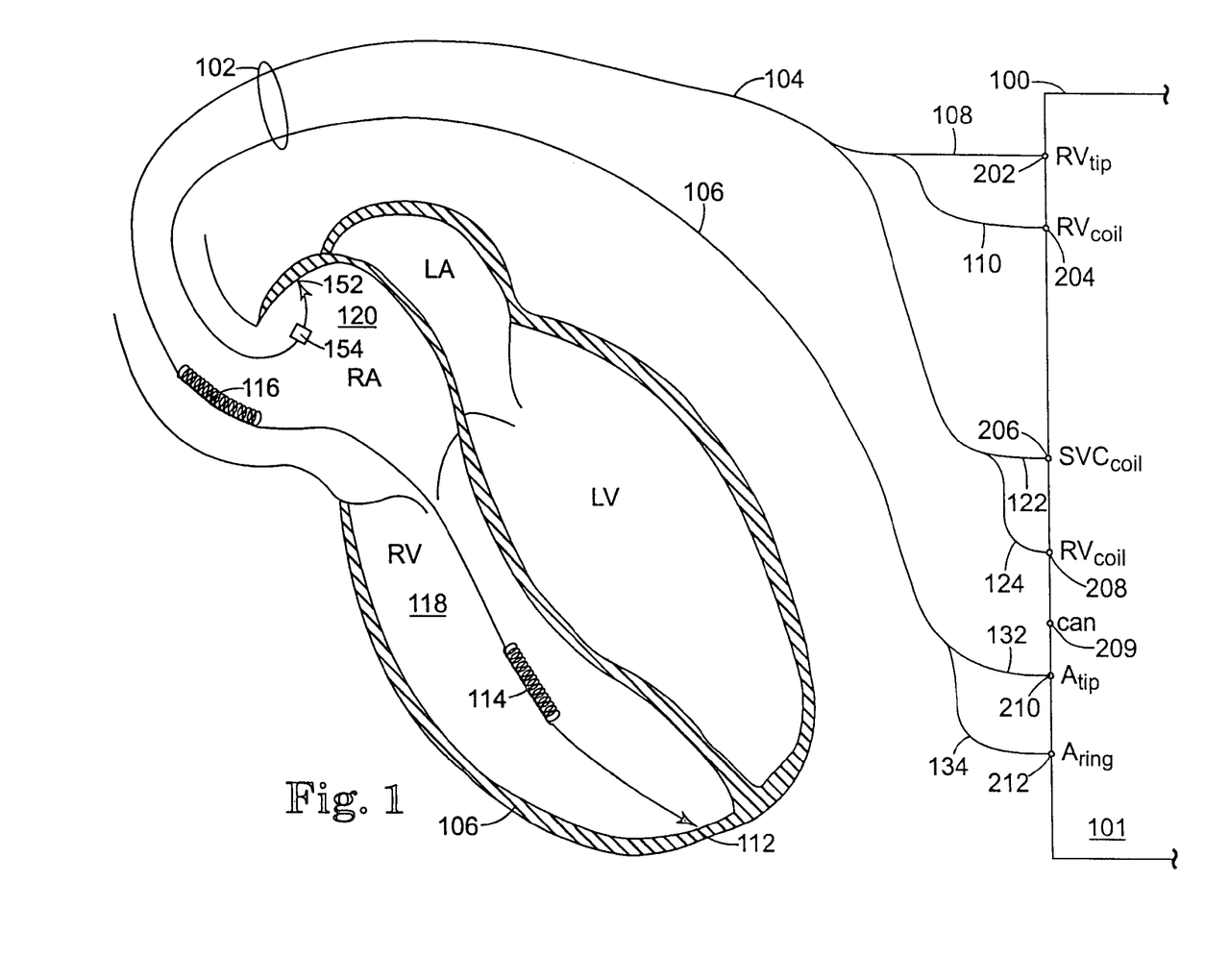
FIG. 1 is a partial view of one embodiment of an implantable medical device with an endocardial lead system extending into right atrial and right ventricular chambers of a heart.

Referring now to FIG. 1 of the drawings, there is shown one embodiment of a medical device system with which the present invention may be implemented. The system includes an implantable cardiac defibrillator 100 electrically and physically coupled to an intracardiac lead system 102. The intracardiac lead system 102 is implanted in a human body with portions of the intracardiac lead system 102 inserted into a heart 106. The intracardiac lead system 102 is used to detect and analyze electric cardiac signals produced by the heart 106 and to provide electrical energy to the heart 106 under certain predetermined conditions to treat cardiac arrhythmias, including, for example, atrial arrhythmias and ventricular arrhythmias associated with ventricular pro-arrhythmia.

The intracardiac lead system 102 includes one or more pacing electrodes and one or more intracardiac defibrillation electrodes. In the particular embodiment shown in FIG. 1, the intracardiac lead system 102 includes a ventricular lead system 104 and an atrial lead system 106. The ventricular lead system 104 includes an SVC-coil 116, an RV-coil 114, and an RV-tip electrode 112. The RV-coil 114, which is also referred to as an RV-ring electrode, is spaced apart from the RV-tip electrode 112, which is a pacing electrode. In one embodiment, the ventricular lead system 104 is configured as an integrated bipolar pace/shock lead. The atrial lead system 106 includes an A-tip electrode 152 and an A-ring electrode 154. In one embodiment, the atrial lead system 106 is configured as an atrial J lead.

In this configuration, the intracardiac lead system 102 is positioned within the heart 106, with a portion of the atrial lead system 106 extending into the right atrium 120 and portions of the ventricular lead system 104 extending into the right atrium 120 and right ventricle 118. In particular, the A-tip electrode 152 and A-ring electrode 154 are positioned at appropriate locations within the right atrium 120. The RV-tip electrode 112 and RV-coil 114 are positioned at appropriate locations within the right ventricle 118. The SVC-coil 116 is positioned at an appropriate location within the right atrium chamber 120 of the heart 106 or a major vein leading to the right atrium chamber 120 of the heart 106. The RV-coil 114 and SVC-coil 116 depicted in FIG. 1 are defibrillation electrodes.

Additional or different pacing and defibrillation electrodes can be included on the intracardiac lead system 102 to allow for various bipolar sensing, pacing, and defibrillation capabilities. For example, the intracardiac lead system 102 may include endocardial pacing and cardioversion/defibrillation leads (not shown) that are advanced into the coronary sinus and coronary veins to locate the distal electrode(s) adjacent to the left ventricle or the left atrium. The distal end of such coronary sinus leads is advanced through the superior vena cava, the right atrium, the valve of the coronary sinus, the coronary sinus, and into a coronary vein communicating with the coronary sinus, such as the great vein. Other intracardiac lead and electrode arrangements and configurations known in the art are also possible and considered to be within the scope of the present system.

Figure 2:
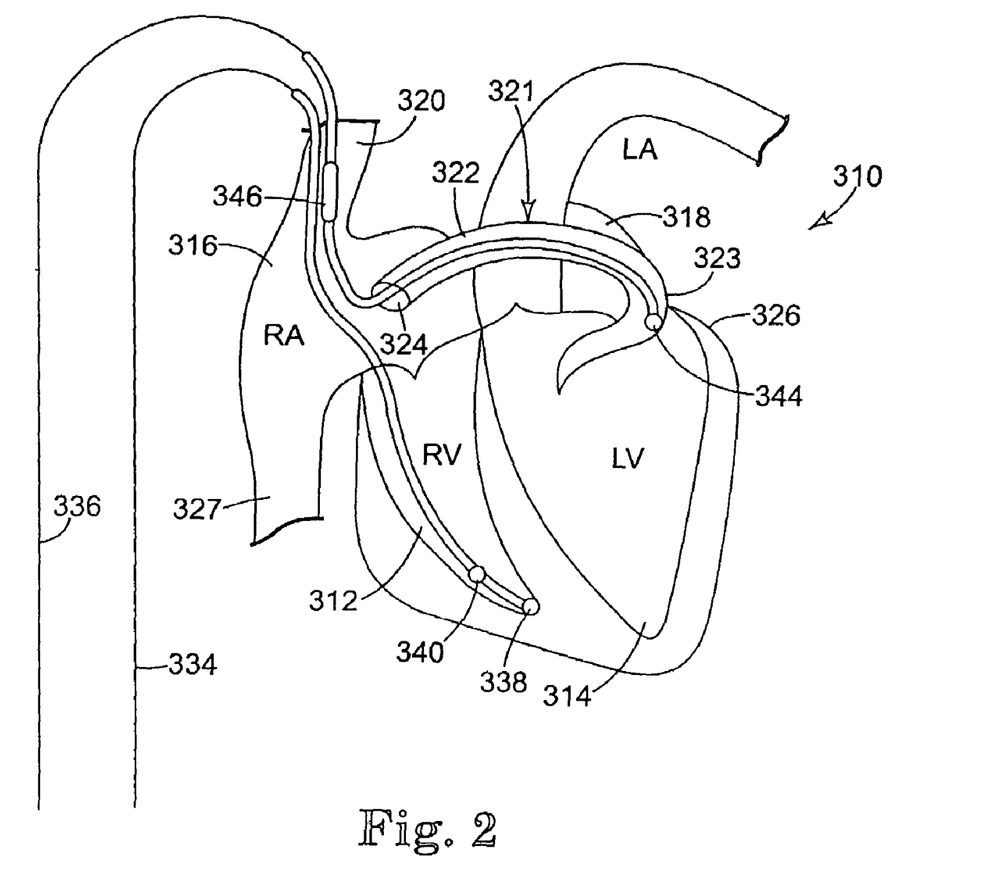
FIG. 2 is a partial view of one embodiment of an implantable medical device with an endocardial lead system extending into right and left atrial and right ventricular chambers of a heart.

By way of particular example, FIG. 2 illustrates another embodiment of an implantable lead system of the type described immediately above. The portions of the heart illustrated in FIG. 2 are the right ventricle 312, the left ventricle 314, the right atrium 316, the left atrium 318, the superior vena cava 320, the coronary sinus channel 321 which, as used herein, denotes the coronary sinus 322 and the great cardiac vein 323, the coronary sinus ostium or opening 324, the left ventricular free wall 326, and the inferior vena cava 327.

Extending into the heart are an endocardial first lead 334 and an intravascular second lead 336. The endocardial first lead 334 preferably comprises an endocardial bi-polar lead having electrodes 338 and 340 arranged for establishing electrical contact with the right ventricle 312 of the heart. The electrodes 338 and 340 permit bi-polar sensing of ventricular activations in the right ventricle. As illustrated, the lead 334 is preferably fed through the superior vena cava 320, into the right atrium 316 and then into the right ventricle 312.

The second lead 336 generally includes a first or tip electrode 344 and a second or proximal electrode 346. As illustrated, the second lead 336 is flexible and arranged to be passed down the superior vena cava 320, into the right atrium 316, into the coronary sinus ostium 324, and advanced into the coronary sinus channel 321 of the heart near the left side thereof so that the first or tip electrode 344 is within the coronary sinus channel 321 either within the coronary sinus 322 adjacent the left ventricle 314 and beneath the left atrium 318 or within the great cardiac vein 323 adjacent the left ventricle 314 and beneath the left atrium 318. The electrodes 344 and 346 are spaced apart such that when the first electrode 344 is positioned as described above, the second electrode 346 is in the right atrium 316.

In this configuration, the first electrode 344 together with the second electrode 346 provide bi-polar sensing of heart activity in the atria 316 and 318. The first electrode 344 and the second electrode 346 further provide for the delivery of defibrillating or cardioverting electrical energy to the atria. The lead arrangement depicted in FIG. 2 may be used in conjunction with the IMD circuitry shown in FIG. 3 or that disclosed in commonly owned U.S. Pat. No. 5,999,851, which is hereby incorporated herein by reference.

Returning now to FIG. 1, the ventricular and atrial lead systems 104, 106 include conductors for communicating sense, pacing, and defibrillation signals between the cardiac defibrillator 100 and the electrodes and coils of the lead systems 104, 106. As is shown in FIG. 1, ventricular lead system 104 includes a conductor 108 for transmitting sense and pacing signals between the RV-tip electrode 112 and an RV-tip terminal 202 within the cardiac defibrillator 100. A conductor 110 of the ventricular lead system 104 transmits sense signals between the RV-coil or ring electrode 114 and an RV-coil terminal 204 within the cardiac defibrillator 100. The ventricular lead system 104 also includes conductors 122, 124 for transmitting sense and defibrillation signals between terminals 206, 208 of the cardiac defibrillator 100 and SVC- and RV-coils 116 and 114, respectively. The atrial lead system 106 includes conductors 132, 134 for transmitting sense and pacing signals between terminals 210, 212 of the cardiac defibrillator 100 and A-tip and A-ring electrodes 152 and 154, respectively.

Figure 3:
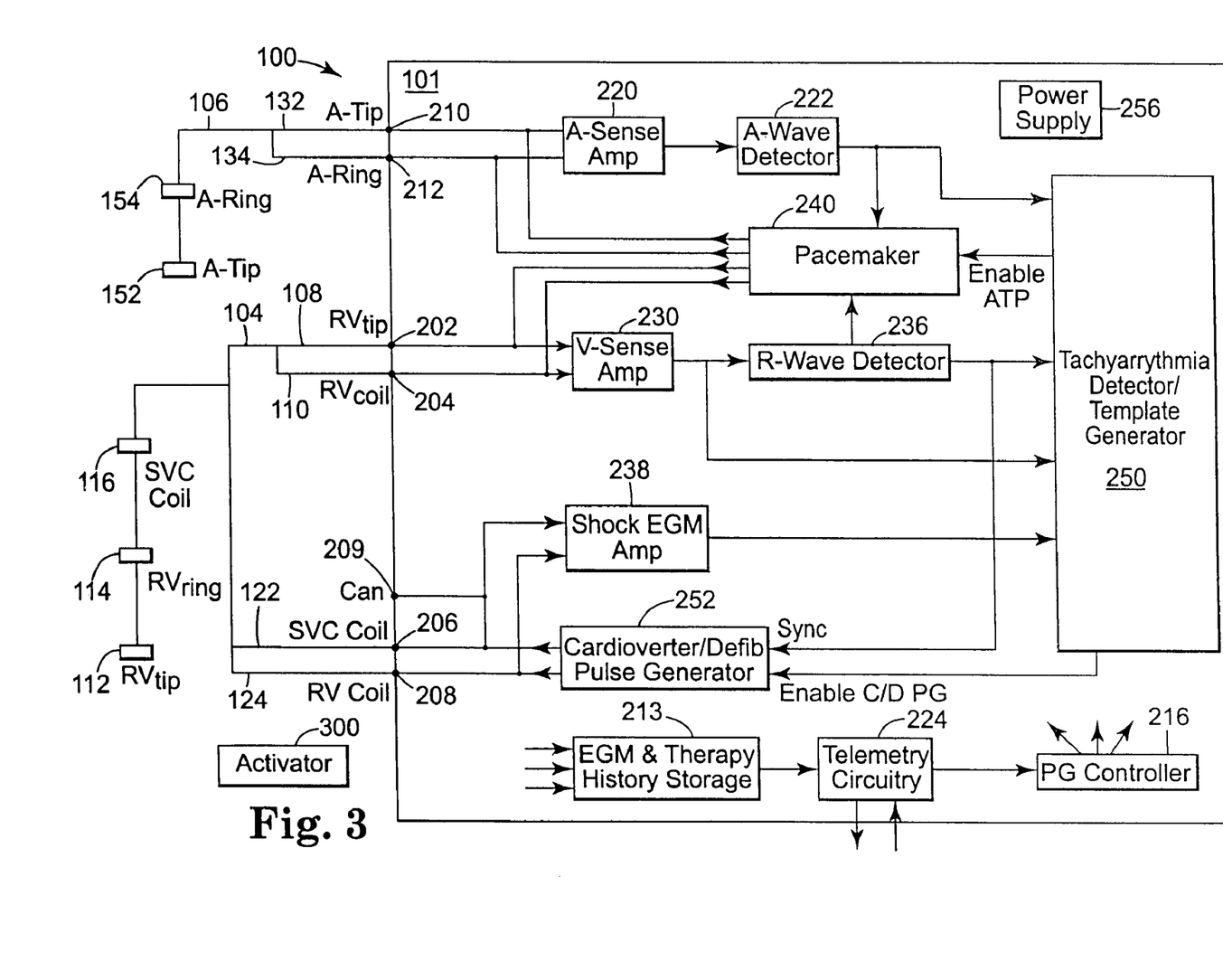
FIG. 3 is a block diagram of a cardiac defibrillator with which a methodology for treating a cardiac arrhythmia of the present invention is implemented.

Referring now to FIG. 3, there is shown an embodiment of a cardiac defibrillator 100 with which embodiments of the present invention may be practiced. The cardiac defibrillator 100 shown in FIG. 3 will be described within the context of the lead arrangement depicted in FIG. 1, it being understood that cardiac defibrillator 100 or variations thereof may also be deployed to accommodate the lead arrangement depicted in FIG. 2 or various other lead arrangements as are known in the art.

The cardiac defibrillator 100 includes control system circuitry 101 for receiving cardiac signals from a heart 106 and delivering electrical energy to the heart 106. The control system circuitry 101 includes terminals 202, 204, 206, 208, 209, 210, and 212 for connecting to the electrodes and coils of the intracardiac lead system 102, as previously discussed.

In one embodiment, the control system circuitry 101 of the cardiac defibrillator 100 is encased and hermetically sealed in a housing 130 suitable for implanting in a human body as is known in the art. Power to the cardiac defibrillator 100 is supplied by an electrochemical battery 256 that is housed within the cardiac defibrillator 100. A connector block (not shown) is additionally attached to the housing 130 of the cardiac defibrillator 100 to allow for the physical and electrical attachment of the intracardiac lead system conductors to the cardiac defibrillator 100 and the encased control system circuitry 101.

In one embodiment, the control system circuitry 101 of the cardiac defibrillator 100 is a programmable microprocessor-based system, with a controller 216 and a memory circuit (not shown). The memory circuit contains parameters for various pacing, defibrillation, and sensing modes and stores data indicative of cardiac signals received by the control system circuitry 101. The controller 216 and memory circuit cooperate with other components of the control system circuitry 101 to perform operations involving the monitoring, moderating, and termination of cardiac arrhythmias that develop during or after delivery of an anti-arrhythmic agent according to the principles of the present invention, in addition to other sensing, pacing and defibrillation functions. A memory 213 is also provided for storing historical EGM and therapy data, which may be used on-board for various purposes and transmitted to an external programmer unit (not shown) as needed or desired.

Telemetry circuitry 224 is additionally coupled to the control system circuitry 101 to allow the cardiac defibrillator 100 to communicate with an external communicating device, such as a hand-held activator 300 or, if appropriate or desired, a programmer unit (not shown). In one embodiment, the telemetry circuitry 224 and the activator 300 use a wire loop antenna and a radio frequency telemetric link, as is known in the art, to receive and transmit signals and data between the activator 300 and the control system circuitry 101. In this manner, various commands, data, and other signals are communicated between the activator 300 and the controller 216 of the cardiac defibrillator 100.

Cardiac signals sensed through use of the RV-tip electrode 112 are near-field signals or rate channel signals as are known in the art. More particularly, a rate channel signal is detected as a voltage developed between the RV-tip electrode 112 and the RV-coil 114. Cardiac signals sensed through use of one or both of the defibrillation coils or electrodes 114, 116 are far-field signals, also referred to as morphology or shock channel signals, as are known in the art. Shock channel signals developed using appropriate combinations of the RV-coil, SVC-coil, and can electrodes 114, 116 and 209 are sensed and amplified by a shock EGM amplifier 238, the output of which is coupled to the tachyarrythmia detector 250.

In the embodiment of the cardiac defibrillator 100 depicted in FIG. 3, RV-tip and RV-coil electrodes 112, 114 are shown coupled to a V-sense amplifier 230. Rate channel signals received by the V-sense amplifier 230 are communicated to an R-wave detector 236. The R-wave detector 236 serves to sense and amplify the rate channel signals (e.g., R-waves) and communicate the detected signals to a pacemaker 240 and a tachyarrythmia detector 250.

A-tip and A-ring electrodes 152, 154 are shown coupled to an A-sense amplifier 220. Atrial sense signals received by the A-sense amplifier 220 are communicated to an A-wave detector 222, which serves to sense and amplify the A-wave signals. The atrial signals are communicated from the A-wave detector 222 to the pacemaker 240 and the tachyarrythmia detector 250. The pacemaker 240 communicates pacing signals to the RV-tip and A-tip electrodes 112 and 152 according to a preestablished pacing regimen under appropriate conditions. Blanking circuitry (not shown) is employed in a known manner when a ventricular or atrial pacing pulse is delivered, such that the ventricular channel, atrial channel, and shock channel are properly blanked at the appropriate time and for the appropriate duration.

The implantable medical devices and non-implantable activator described with reference to FIGS. 1-3 are well-suited for implementing embodiments of the present invention. An embodiment of the activator 300 shown in FIG. 3 is depicted in greater detail in FIG. 4. According to the embodiment shown in FIG. 4, a non-implantable activator 300 is provided in a housing 360 configured for portability and ease of use by the patient. The activator 300 includes a display 362, such as an LCD display, a speaker 374, and a vibration unit 380 for communicating visual, aural, and tactile information, respectively, to the patient. A controller 384, such as a microprocessor, and memory 382 are provided within the housing 360. A battery 378 provides power to the active components of the activator 300.

Figure 4:
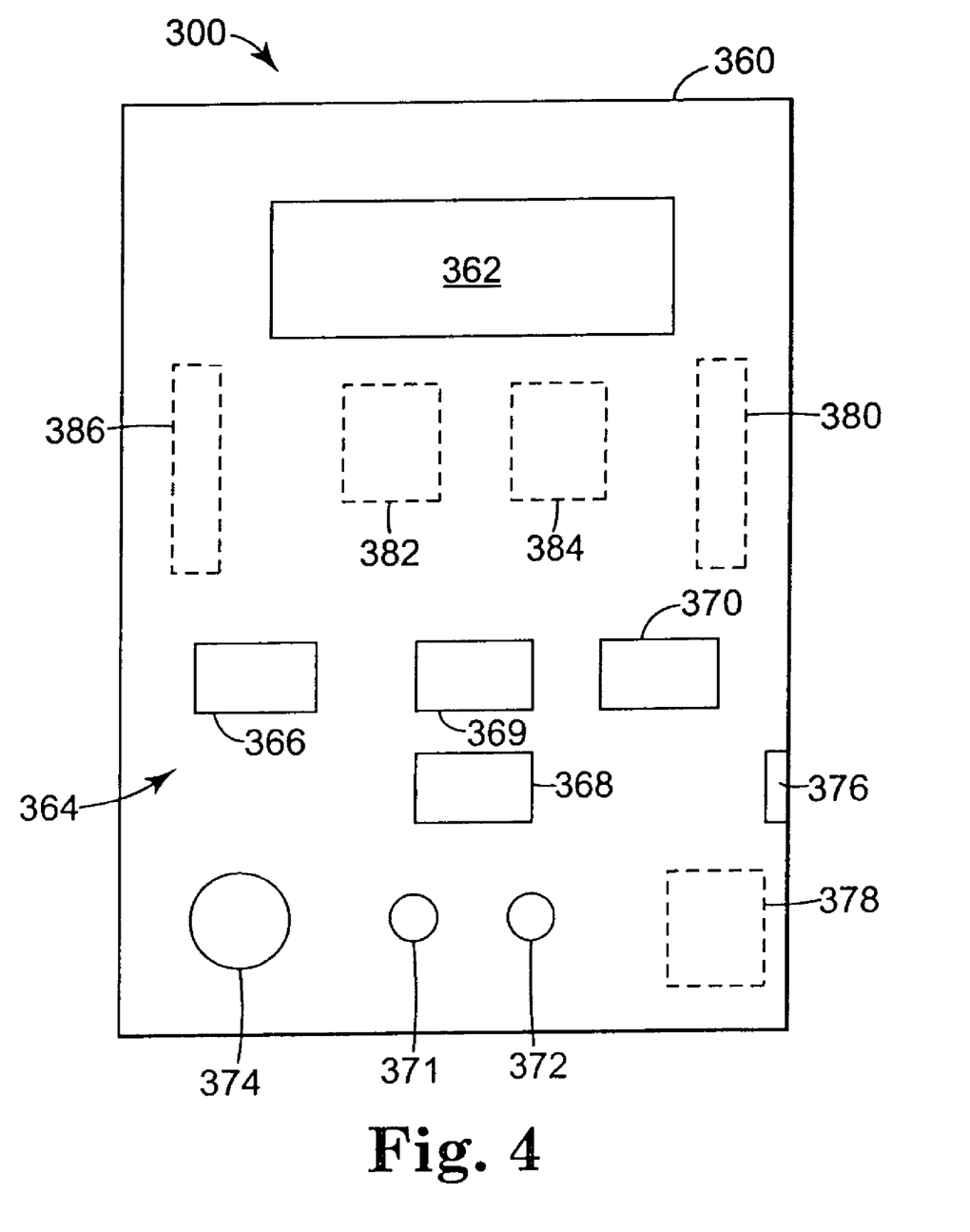
FIG. 4 shows a non-implantable activator that operates in cooperation with an implantable medical device in accordance with an embodiment of the present invention.

A control panel 364 is provided on the housing 360 and includes a number of user actuatable switches. As shown, the control panel 364 of the activator 300 includes a mode switch 366 and a status query switch 370. The mode switch 366 provides for user selectability between various activator operational modes and, in particular, a number of pacing modes. The status query switch 370 provides for the presentation of various types of status information, including, for example, implantable medical device status data, patient physiology data, and activator related data.

An activation LED 372 provides a visual indication that the patient has activated the cardiac arrhythmia response capabilities provided to the patient, such as electrical cardioversion capabilities provided by the implantable medical device and chemical cardioversion capabilities to be administered by the patient. In response to the patient sensing onset of a perceived cardiac arrhythmic condition, the activation switch 368 is actuated by the patient, which results in illumination of activation LED 372. Illumination of activation LED 372 unambiguously indicates the patient's perception of the onset of a cardiac arrhythmic episode and the patient's intent to initiate the anti-arrhythmia capabilities made available to the patient.

The activator 300 communicates with the implantable medical device via a transceiver 386, which includes an antenna. The transceiver 386 communicates with the telemetry circuitry of the implantable medical device to uplink and downlink information therebetween in a manner known in the art. The implantable medical device, for example, receives an activation signal that is generated by the controller 384 and transmitted by the transceiver 386 of the activator 300. The activation signal is received by the implantable medical device, which confirms the presence of an actual cardiac arrhythmia. If an actual cardiac arrhythmia is confirmed, the implantable medical device transmits a confirmation signal to the activator 300, which is received by transceiver 386. A message is presented on display 362 of the activator 300 to communicate to the patient that the implantable medical device has detected an actual cardiac arrhythmia. The activation LED 372 or other LED may also illuminate in a particular manner or color to alert the patient that the perceived cardiac arrhythmia has been confirmed as an actual arrhythmic event.

Upon confirming an actual cardiac arrhythmic condition, an initiation LED 371 is illuminated to instruct the patient that a prescribed drug regimen is to be administered. The activation LED 372 may be deactivated upon illumination of the initiation LED 371. It is understood that activation and initiation LEDs 372, 371 may be substituted by use of a single LED or other annunciator capable of transitioning between at least two visually perceivable states (e.g., color states, illumination or blinking states).

A communications interface 376, such as a network interface connector or wireless communications interface, provides for connectivity between the portable activator 300 and a network. The communications interface 376 provides the ability to communicate stored information acquired by the activator 300 and the patient's implantable medical device to a physician's office or hospital for evaluation.

The communications interface 376 also allows the physician to obtain real-time information (e.g., electrocardiogram, physiologic, IMD/activator operational data) via an active communications link established between the network, activator 300 (via communications interface 376), and implantable medical device (via transceiver 386). Further, the physician may also send instructions (e.g., commands, software changes and updates) to the activator 300 and/or implantable medical device to alter the operation of the activator 300 and/or implantable medical device.

The switch panel 364 of the activator 300 may also include a drug data switch 369. The drug data switch 369 provides for the selection and presentation of various drug related data on the display 362. The drug related data may, for example, indicate the required or recommended drug of a drug regimen to be administered by the patient in response to the implantable medical device confirming the onset of an actual cardiac arrhythmic condition. Logic of the activator 300 may suggest a prioritized listing of drugs and/or drug dosages to be delivered based on a physician's recommendation or prescription. The drug recommendation and/or drug dosage may be adjusted by the activator logic in response to the actual cardiac arrhythmic condition sensed by the implantable medical device.

In this regard, real-time data acquired by the implantable medical device may be used by the activator 300 to refine activator recommendations concerning drug dosages, time between dosage deliveries, and specific drugs. Also, the patient may be provided with severity information, such that the relative severity of the arrhythmic condition is communicated to the patient, including, for example, warnings that immediate physician intervention is required.

The controller 384, memory 382, display 362, and switches of the control panel 364 (several of which are not shown, such as enter, scroll, and cursor movement keys) provide for user friendly navigation of menus and functions provided by the activator 300. These and other components of the activator 300 described above may be modified in form and function depending on the requirements of the system. For example, several of the above described components and functions may be included or excluded depending on the system design requirements.

Figure 5:
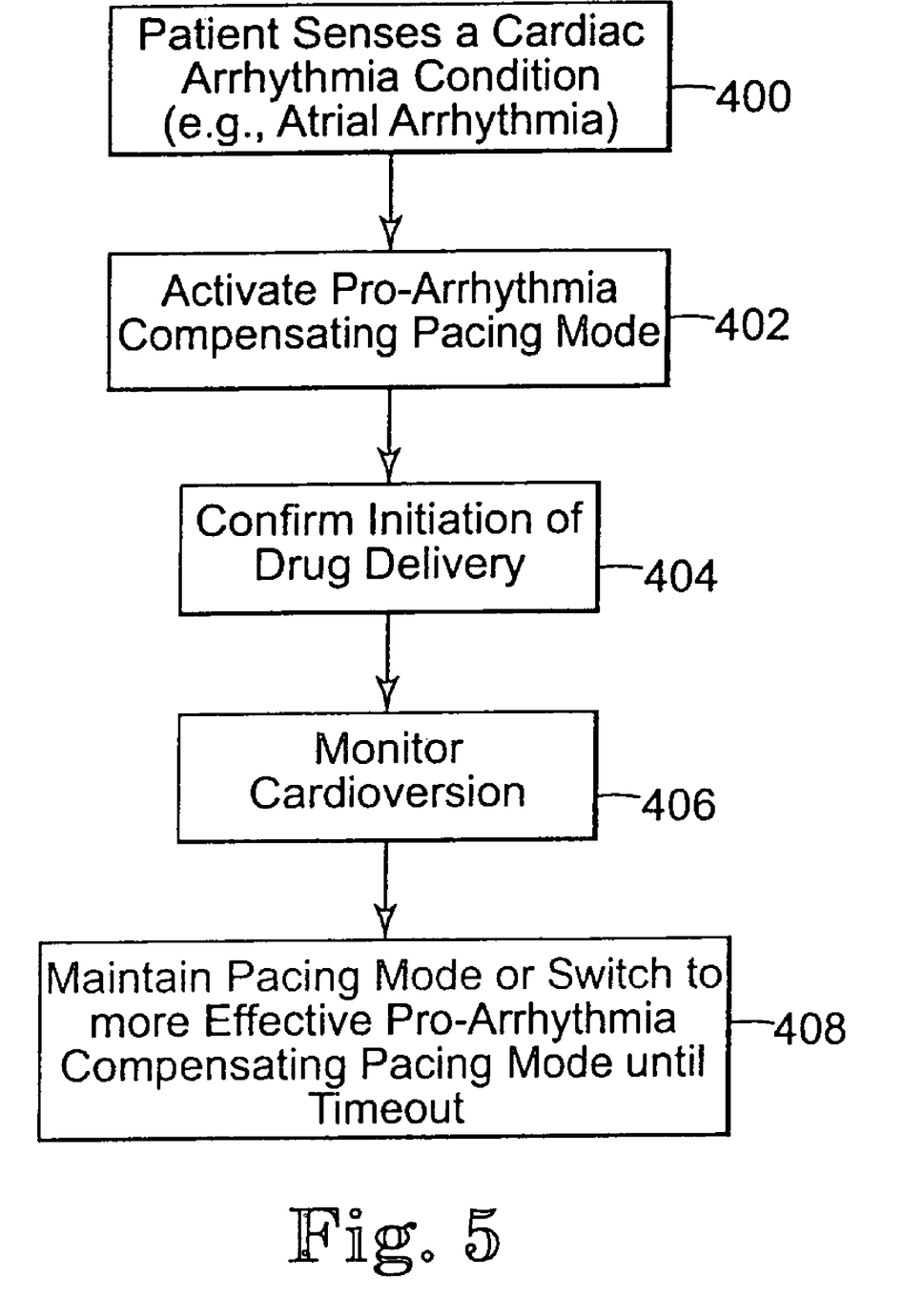
FIG. 5 depicts various processes involving the prevention or termination of a cardiac arrhythmic condition associated with the administering of chemical and electrical cardioversion in accordance with an embodiment of the present invention.

Turning now to FIG. 5, there is illustrated various processes involving the prevention or termination of a cardiac arrhythmic condition associated with the administering of chemical cardioversion. In this embodiment, the patient is viewed as a sensor, in that the patient can typically sense 400 the onset or presence of a cardiac arrhythmia. Alternatively, the implantable medical device provided within the patient may sense 400 the onset or presence of a cardiac arrhythmia.

In response to sensing the onset or presence of a cardiac arrhythmia, a pro-arrhythmia compensating pacing mode is activated 402. Such a pacing mode is one that accounts for the increased risk of an arrhythmia developing during the effectiveness period of a particular drug delivered to the patient. The patient confirms 404 that the prescribed drug has been administered (e.g., via oral, intravenous, skin patch, nasal, or other means). The chemical cardioversion procedure is monitored 406. The pacing mode is maintained, or a more effective mode is selected, until a predefined time duration has expired 408. A standard pacing mode may be selected and initiated after the risk of pro-arrhythmia has reduced.

Figure 6:
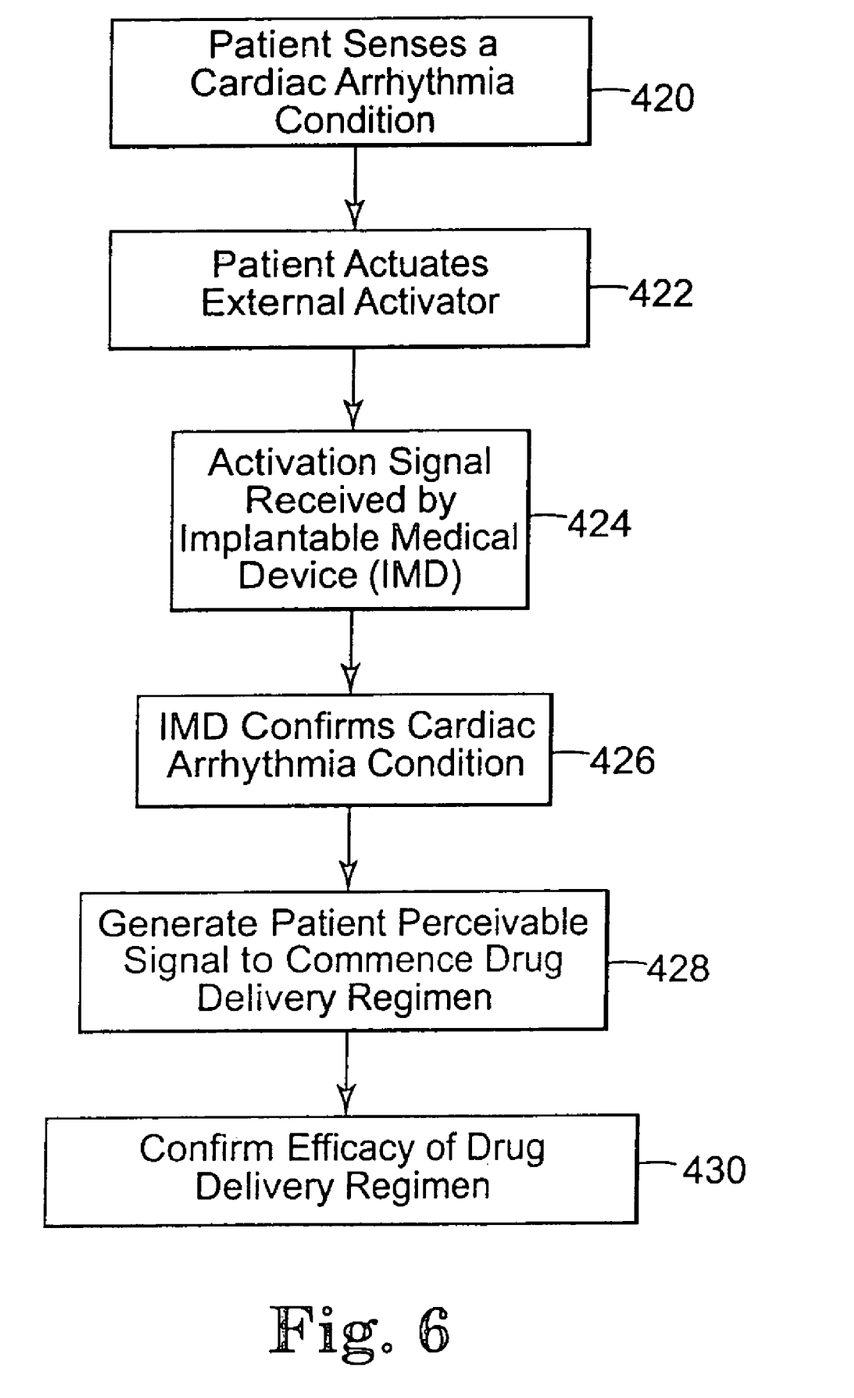
FIG. 6 depicts various processes involving the prevention or termination of a cardiac arrhythmic condition associated with the administering of chemical cardioversion in accordance with an embodiment of the present invention.

FIG. 6 depicts various processes involving the prevention or termination of a cardiac arrhythmic condition associated with the administering of chemical cardioversion in accordance with another embodiment of the present invention. In this embodiment, the patient or implantable medical device senses 420 a cardiac arrhythmic condition. The patient then actuates 422 an external activator. The activator generates an activation signal which is received 424 by the implantable medical device. The implantable medical device confirms 426 the presence of a cardiac arrhythmic condition, such as by monitoring the time between successive R-waves, referred to as RR intervals, or by other means known in the art. For example, an RR interval may be measured as an interval between Vs to Vs, Vs to Vp, Vp to Vs, or Vp to Vp events, where Vs is the ventricular sensed event detection time and Vp is the ventricular pace pulse delivery time.

The implantable medical device generates and transmits a confirmation signal in response to confirming an actual arrhythmic condition. The confirmation signal transmitted by the implantable medical device is received by the external activator. An initiation signal perceivable by the patient is produced 428 by the external activator in response to the received confirmation signal. The initiation signal is preferably a visual signal (LED, message display, icon display, etc.), but may also be an audio or tactile signal, or a combination of these signal types. The patient, in response to the initiation signal, is prompted to commence 428 the prescribed drug delivery regimen. The implantable medical device monitors 430 the effectiveness of the drug delivery regimen. The efficacy of the administered cardioversion drug regimen is communicated in visual or auditory form to the patient, typically on a repeated basis over the duration of the chemical cardioversion procedure. The patient may, for example, query the implantable medical device using the external activator to obtain various types of data relating to the chemical cardioversion procedure.

Figure 7:
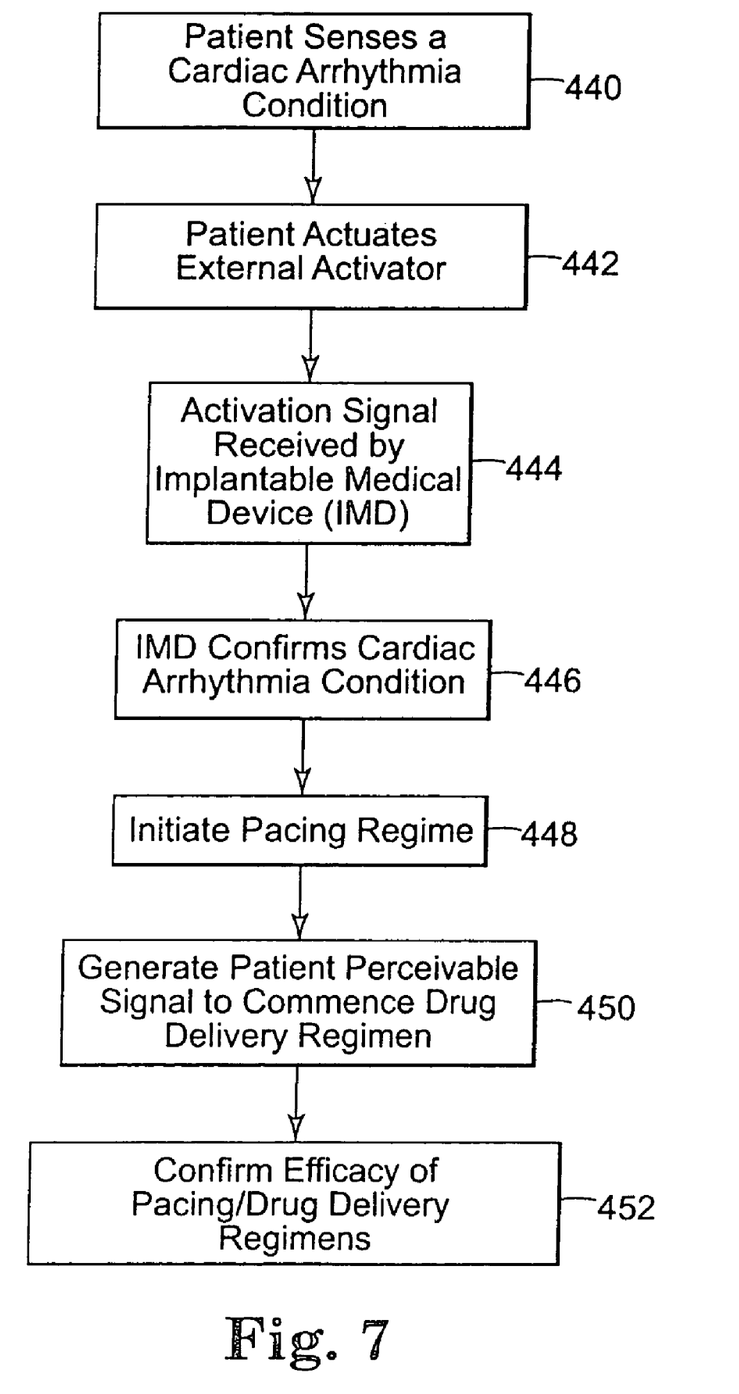
FIG. 7 depicts various processes involving the prevention or termination of a cardiac arrhythmic condition associated with the administering of chemical and electrical cardioversion in accordance with another embodiment of the present invention.

FIG. 7 depicts various processes involving the prevention or termination of a cardiac arrhythmic condition associated with the administering of chemical cardioversion in accordance with a further embodiment of the present invention. As in the embodiment depicted in FIG. 6, the patient or implantable medical device senses 440 a cardiac arrhythmic condition and, in response, actuates 442 an external activator. The activation signal generated by the activator is received 444 by the implantable medical device. The implantable medical device confirms 446 the presence of a cardiac arrhythmic condition.

According to this embodiment, the implantable medical device initiates 448 a pacing regime appropriate for the patient and the type of chemical cardioverting drugs that the patient or doctor will be administering. An appropriate pacing regime is one that reduces the risk of an arrhythmia developing during the effectiveness period of a particular drug delivered to the patient.

The implantable medical device transmits a confirmation signal to the external activator in response to confirming an actual arrhythmic condition. The external activator generates 450 an initiation signal perceivable by the patient in response to the received confirmation signal. The patient, in response to the initiation signal, is prompted to commence 450 the prescribed drug delivery regimen. The implantable medical device monitors 452 the effectiveness of the drug delivery regimen and communicates the efficacy of the administered cardioversion drug regimen to the patient.

Devices and methods implemented in accordance with the principles of the present invention can be employed to treat a wide variety of adverse cardiac conditions in addition to those discussed hereinabove. Such adverse cardiac conditions include both arrhythmic and non-arrhythmic conditions, including heart failure conditions, decompensation events, tachycardia conditions, bradycardia conditions, acute ischemic events (e.g., myocardial infarction), and episodes of angina, for example.

In the context of an embodiment of the present invention, it is assumed that a patient who is susceptible to one or more of these or other adverse cardiac condition(s) is currently being treated with an appropriate drug delivery regimen as prescribed by a physician. In addition, it is assumed that a cardiac management device implanted in the patient has been programmed, or is capable of being dynamically programmed, to operate in one or more safe pacing modes appropriate for one or more particular adverse cardiac conditions and appropriate for the prescribed drug delivery regimen.

Figure 8:
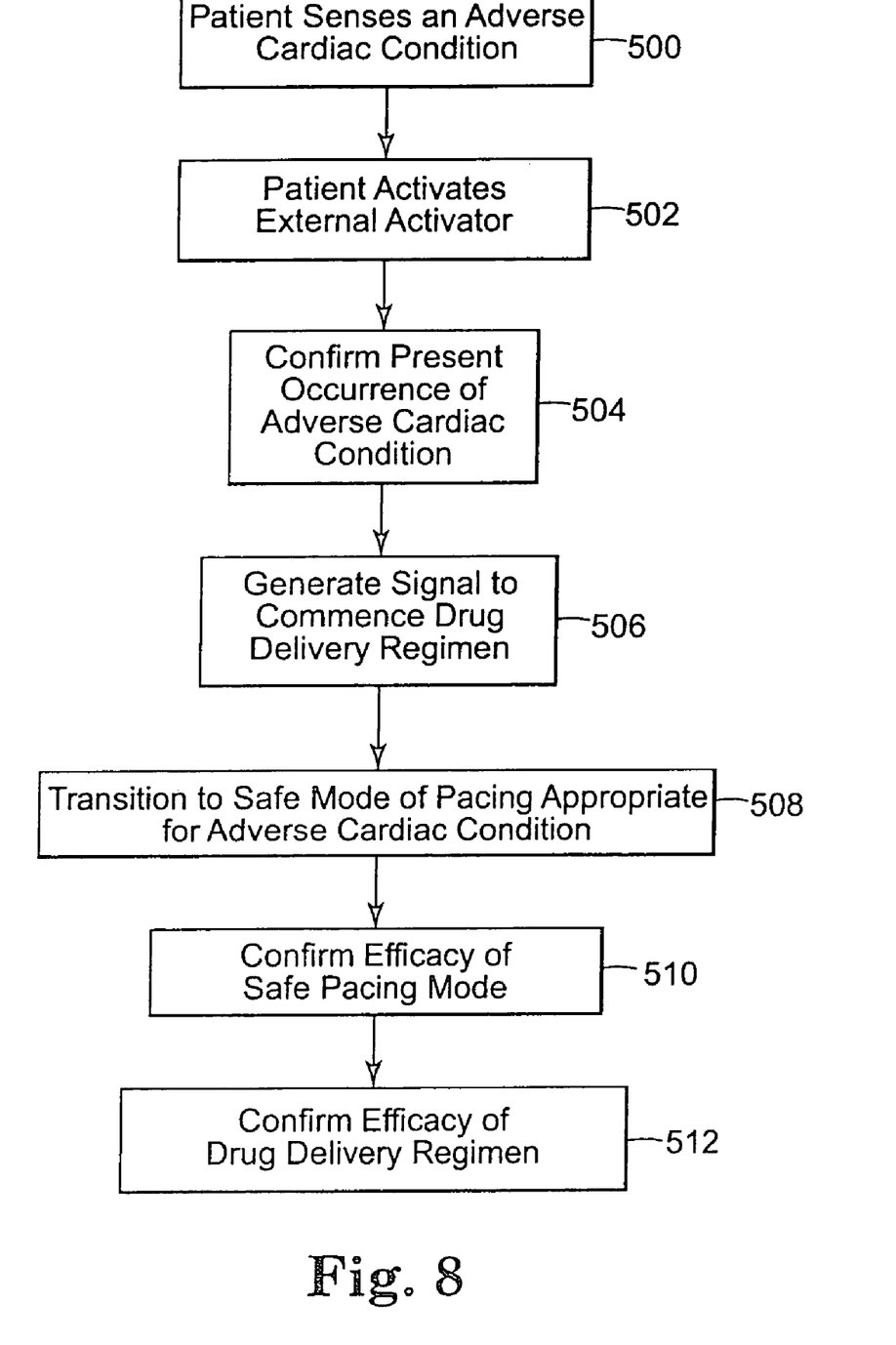
FIG. 8 depicts various processes involving the detection and confirmation of an adverse cardiac condition, and transitioning to a safe mode of pacing appropriate for the detected adverse cardiac condition in accordance with another embodiment of the present invention.

FIG. 8 depicts various processes involving the detection and confirmation of an adverse cardiac condition experienced by a given patient, and the patient-assisted transitioning of an implanted cardiac management device to a safe mode of pacing appropriate for the detected adverse cardiac condition and prescribed drug therapy in accordance with an embodiment of the present invention. The processes shown in FIG. 8 are initially implicated when a patient senses 500 an adverse cardiac condition, such as one of the adverse cardiac events listed above. In response to perceiving the adverse cardiac condition, the patient activates 502 an external activator in a manner previously described.

The implanted cardiac management device, in response to patient activation of the external activator, confirms 504 that the patient is experiencing an actual adverse cardiac condition. Upon confirming the present occurrence of the adverse cardiac condition, the implanted cardiac management device generates 506 a signal indicating that a drug delivery regimen is to be commenced (e.g., taking of nitroglycerin in the case of a myocardial infarction event). The external activator receives this signal and, in response, communicates a drug delivery commencement message (e.g., audio, visual, and/or tactile message) to the patient.

In the case of congestive heart failure, for example, the patient may be directed by the external activator to take an ACE inhibitor, β-blocker, diuretic or dosage of spironalactone, for example, as prescribed by the patient's physician. In the case of angina or myocardial infarction, by way of further example, the external activator may direct the patient to take aspirin, nitroglycerin or other drug that dilates heart vessels as previously prescribed.

The implanted cardiac management device transitions 508 to a safe pacing mode appropriate for the detected adverse cardiac condition and the drug therapy delivered to the patient. The implanted cardiac management device determines 510 whether or not the safe pacing mode is effecting proper pacing of the heart to treat the detected adverse cardiac condition. The implanted cardiac management device can transition to another pacing mode if the current pacing mode is not effectively treated the adverse cardiac condition.

In the case of certain adverse non-arrhythmic cardiac conditions, such as an episode of angina, a heart failure decompensation event or myocardial infarction, for example, the implanted cardiac management device transitions 508 to a safe pacing mode which provides for an increase in pumping efficiency of the heart. For example, the implanted cardiac management device can transition to a left ventricular pacing mode or a bi-ventricular pacing mode as is known in the art for purposes of increasing the hemodyamic efficiency or output of the heart.

Subsequent to the patient taking the prescribed medication, the implanted cardiac management device monitors cardiac activity to confirm 512 that the drug delivery regimen is effectively treating the adverse cardiac condition. For example, the implanted cardiac management device continues operating in the safe pacing mode(s) and monitoring cardiac activity for a duration of time equal to or exceeding several half-lives of the drug or drugs taken by the patient as part of the prescribed drug delivery regimen. Assuming that the adverse cardiac condition has been effectively treated, such as by not detecting the reoccurrence of the adverse condition for several drug half-lives, the implanted cardiac management device can transition to normal pacing mode programming specified for the patient.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of safely pacing a patient's heart when administering a drug therapy to a patient, the method comprising:
   detecting that the patient is experiencing an adverse cardiac condition;
   confirming, at least in part by an implantable cardiac management device provided within the patient, that the patient is experiencing an actual adverse cardiac condition;
   generating, by a non-implantable portable communications device, a signal instructing the patient or a physician to commence delivery of a drug regimen to treat the actual adverse cardiac condition;

initiating a safe pacing mode by the implantable cardiac management device appropriate for the drug regimen delivered to the patient and the detected adverse cardiac condition; and continuing the safe pacing mode for at least a period of time during which the delivered drug regimen could influence the patient's cardiac activity.

2. The method of claim 1, wherein the drug regimen is delivered to treat the adverse cardiac condition and the safe pacing mode comprises an anti pro-arrhythmia pacing mode that reduces the risk of provoking a new arrhythmia or aggravating a pre-existing arrhythmia during delivery of the drug regimen at doses or plasma concentrations below those considered toxic.

3. The method of claim 1, wherein the drug regimen is delivered to treat the adverse cardiac condition and the safe pacing mode comprises a pacing mode that attempts to maintain proper pacing of the heart during the period of time in which the delivered drug regimen could influence the patient's cardiac activity.

4. The method of claim 1, wherein the drug regimen comprises a chemical for treating an atrial arrhythmic cardiac condition, and the safe pacing mode comprises a pacing mode that reduces the risk of a ventricular arrhythmia developing during the period of time in which the delivered drug regimen could influence the patient's cardiac activity.

5. The method of claim 1, wherein the drug regimen comprises a chemical for treating a non-arrhythmic cardiac condition, and the safe pacing mode comprises a pacing mode that enhances pumping efficiency of the patient's heart during the period of time in which the delivered drug regimen could influence the patient's cardiac activity.

6. The method of claim 1, comprising communicating information between the portable communications device and a network communicatively coupled to the portable communications device.

7. The method of claim 1, comprising effecting communication between the implantable cardiac management device and the network via the portable communications device.

8. The method of claim 7, comprising transmitting at least one of instructions, commands, and software changes from the network to the portable communications device.

9. The method of claim 7, comprising transmitting at least one of instructions, commands, and software changes from the network to the implantable cardiac management device via the portable communications device.

10. The method of claim 1, comprising:

communicating information regarding the detected adverse cardiac condition between the implantable cardiac management device and the portable communications device;

communicating information between the portable communications device and a network communicatively coupled to the portable communications device;

transmitting a signal from the network to the portable communications device; and adjusting operation of the portable communications device in response to the transmitted signal.

11. The method of claim 10, comprising receiving an input from a physician, wherein the signal is generated in response to the physician input.

12. The method of claim 1, comprising:

communicating information regarding the detected adverse cardiac condition between the implantable cardiac management device and the portable communications device;

communicating information between the portable communications device and a network communicatively coupled to the portable communications device;

transmitting a signal from the network to the portable communications device; and adjusting operation of the implantable cardiac management device in response to the transmitted signal.

13. The method of claim 12, comprising receiving an input from a physician, wherein the signal is generated in response to the physician input.

14. A medical system, comprising:

an implantable cardiac management device comprising:
 a communications unit;
 a detector configured to detect cardiac electrical activity;
 an energy delivery system;
 a lead system coupled to the detector and the energy delivery system; and
 a control system coupled to the communications unit, the detector, and the energy delivery system, the control system configured to operate in a plurality of energy delivery modes, the plurality of energy delivery modes comprising at least a safe pacing mode; and a non-implantable portable communications device, comprising:
 a housing configured for portability by the patient;
 communication circuitry supported by the housing and configured to effect communications with the implantable cardiac management device;
 a user interface supported by the housing; and
 a controller supported by the housing and coupled to the communication circuitry and the user interface;

wherein the system confirms, at least in part by use of the implantable cardiac management device, that the patient is experiencing an actual adverse cardiac condition, and the portable communications device generates an instruction via the user interface instructing the patient or a physician to commence delivery of a drug regimen to treat the actual adverse cardiac condition, the control system of the implantable cardiac management device initiating a safe pacing mode appropriate for the drug regimen delivered to the patient and the detected adverse cardiac condition and continuing the safe pacing mode for at least a period of time during which the delivered drug regimen could influence the patient's cardiac activity.

15. The system of claim 14, wherein the safe pacing mode comprises an anti pro-arrhythmia pacing mode that reduces the risk of provoking a new arrhythmia or aggravating a pre-existing arrhythmia during delivery of the drug regimen at doses or plasma concentrations below those considered toxic.

16. The system of claim 14, wherein the drug regimen comprises a chemical for treating an atrial arrhythmic cardiac condition, and the safe pacing mode comprises a pacing mode that attempts to maintain proper pacing of the heart during the period of time in which the delivered drug regimen that treats the adverse cardiac condition could influence the patient's cardiac activity.

17. The system of claim 14, wherein the drug regimen comprises a chemical for treating a non-arrhythmic cardiac condition, and the safe pacing mode comprises a pacing mode that enhances pumping efficiency of the patient's heart during the period of time in which the delivered drug regimen could influence the patient's cardiac activity.

18. The system of claim 14, wherein the communication circuitry of the portable communications device comprises:
- a first communications circuit configured to effect communications with the implantable cardiac management device; and
- a second communications circuit configured to effect communications with a network.

19. The system of claim 18, wherein the controller receives information from the network via the second communications circuit, the controller adjusting operation of the portable communications device in response to the received signal.

20. The system of claim 18, wherein the controller receives information from the network via the second communications circuit, the controller adjusting operation of the implantable cardiac management device in response to the received signal.

* * * * *